United States Patent [19]

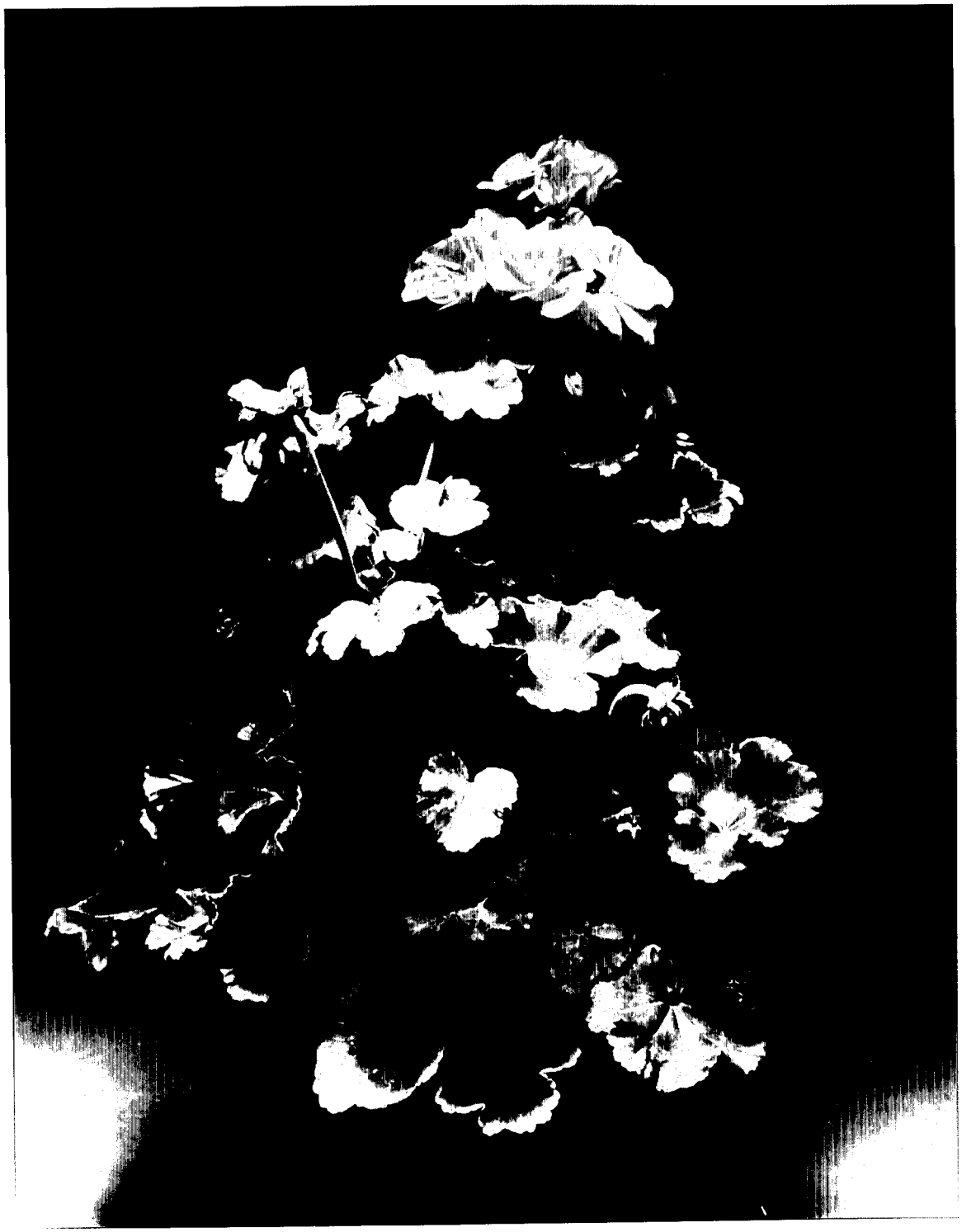

Buck

[11] Patent Number: Plant 5,758

[45] Date of Patent: Jul. 1, 1986

[54] GERANIUM PLANT NAMED TROUBADOUR

[75] Inventor: Griffith J. Buck, Ames, Iowa

[73] Assignee: Iowa State University Research Foundation, Inc., Ames, Iowa

[21] Appl. No.: 673,103

[22] Filed: Nov. 19, 1984

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Tilton, Fallon, Lungmus

[57] ABSTRACT

A new variety of geranium plant distinguished by the bright scarlet color of its flowers, its ability to grow vigorously and flower profusely under high day/night temperatures and humidity, and its tolerance under field conditions to foliar diseases common to geraniums.

1 Drawing Figure

BACKGROUND OF THE NEW PLANT

This cultivar originated as a seedling produced by crossing "Hazel" (U.S. Plant Pat. No. 4,040) as the pollen parent with an unnamed variety in my stock resulting from crossing "Skylark" with "Waltztime" (both unpatented) as the seed parent. The new variety was discovered by me at Iowa State University Horticulture Greenhouses, Ames, Iowa, in 1978 and resulted from breeding efforts commenced by me in 1956 at that University. The new plant was selected for propagation because of its tolerance to high day and night temperatures and high humidity conditions, its ability to grow vigorously and flower profusely under those conditions, its bright scarlet color, and its high tolerance under field conditions to foliar diseases such as *Botrytis cinerea*. Propagation was carried out under my direction at Iowa State University, Ames, Iowa, by means of cuttings and has been continued through successive generations to demonstrate that the distinctive characteristics of the plant are reproducible from generation to generation.

DESCRIPTION OF THE DRAWING

This new varietal is illustrated by the accompanying photographic drawing which shows an entire plant, including its blooms, buds, and foliage, in full color, with such colors of the photograph being as true to those of the plant as can be reasonably obtained with conventional professional photographic procedures.

DESCRIPTION OF THE NEW PLANT

The following is a description of my new geranium plant variety with color designations according to The Royal Horticultural Society Colour Chart (R.H.S.C.C.).

THE PLANT

Origin: Seedling.

Parentage:

*Seed parent.*—An unnamed variety obtained by crossing "Skylark" with "Waltztime" (both unpatented).

*Pollen parent.*—"Hazel" (U.S. Plant Pat. No. 4,040).

Classification:

*Botanic.*—*Pelargonium hortorum.*

*Commercial.*—Garden geranium.

Form: Bush.

Size: 35 to 45 cm. high and 35 to 45 cm. wide (30×30 cm. as a four inch pot plant).

Growth: Vigorous, upright, and branching.

Strength: Sturdy with notable resistance to breaking apart when exposed to wind and rain.

Foliage: Abundant quantity.

*Leaves.*—Size: About 10 to 13 cm. in diameter. Shape: Round-cordate with several rounded lobes and serrate margins. Texture: Leathery and slightly pubescent on both surfaces which feel firm to the touch. Color: Upper side: Dark Yellow-Green 146A (R.H.S.C.C.) with indistinct center zone of lighter Yellow-Green 146B (R.H.S.C.C.). Under side: Medium dark Yellow-Green 146B (R.H.S.C.C.). Ribs and veins: Conspicuous on under side of leaf, but not prominent on upper surface.

Petioles: 9.5 to 10.5 cm. long.

THE BUD

Size: Large, having a length of about 1.5 to 2.1 cm. and a diameter of about 0.7 to 0.9 cm.

Shape: Pointed ovoid.

Opening: Bud opens slowly.

Color:

*When sepals first divide.*—Signal Red 43A (R.H.S.C.C.); when petals begin to unfurl, Scarlet Red 43B (R.H.S.C.C.).

Sepals: Separated spear-shaped sepals that stand up and then curl back with age. Their inside color is Lettuce Green 144A (R.H.S.C.C.), developing a red tinge with age.

THE FLOWER

Blooming habit: Continuous and profuse throughout summer; under glass and with adequate photoperiod and temperatures, it will bloom continuously throughout the year.

Size: Very large. Diameter is 13 to 15 cm., depth is 6 to 8 cm.

Borne: Inflorescence is an umbel and is borne singly.

Shape: Compact; somewhat globular.

Florets:

*Form.*—Cup-shaped when the bloom first opens, later flattening with maturity.

*Petals.*—6 to 8 in number; form is obovate, arrangement is imbricate and appearance is satiny.

*Color.*—Both the outer and inner petals are Signal Red 43A (R.H.S.C.C.) with the outer petals having white claws at their bases. The reverse sides of the petals are Scarlet Red 43B (R.H.S.C.C.). The petals darken with age.

*Petaloids.*—2 to 3 in number with sizes ranging from 2.0 to 2.2 cm. long and 0.7 to 0.9 cm. wide. Their color is Signal Red 43A (R.H.S.C.C.).

*Persistence.*—Flowers hang on and dry with a lasting quality on the plant of 5 to 7 days and about the same length of time as cut flowers.

*Disease resistance.*—Plant is tolerant of foliar diseases common to geraniums, particularly *Botrytis cinerea.*

REPRODUCTIVE ORGANS

Stamens:

*Anthers.*—7 to 10 in number.

*Length.*—About 3.0 to 3.5 mm.

*Filaments.*—4 to 7 mm. in length.

*Color.*—White.

*Pollen.*—Color — Brownish yellow.

Pistils:

*Number.*—One.

*Length.*—7 to 10 mm.

*Stigmas.*—Color — Pale Scarlet 44D (R.H.S.C.C.).

Ovaries: 5 celled.

Fruit: Partially fertile.

*Shape.*—Ovoid with a long "beak".

*Color.*—Brownish-black at maturity.

This variety of geranium cultivar is similar in plant habit to "Pearlie Mae" (U.S. Plant Pat. No. 4,039), and also to that of its pollen parent "Hazel" (U.S. Plant Pat. No. 4,040) in that it is tolerant of high day and night temperatures and humidity and is able to grow vigorously and flower profusely under those climatic conditions. The flower color is similar to that of "Troubadour" except that it is somewhat brighter and more intense. This cultivar also retains the desirable traits of its parents with its profuse flowering resulting in part from its ability to initiate inflorescence on a 2 to 4 node cycle. The cultivar also shows a high tolerance under field conditions to foliar diseases such as *Botrytis cinerea* (Gray Mold).

I claim:

1. A new and distinct geranium variety substantially as herein shown and described, characterized by its abundant production of umbel-formed clusters of very large florets, the strong red coloring of its flowers, and its resistance to foliar diseases, particularly *Botrytis cinerea.*

* * * * *